(12) United States Patent
Waldner et al.

(10) Patent No.: US 6,338,822 B1
(45) Date of Patent: Jan. 15, 2002

(54) OPTICAL CARBON DIOXIDE SENSORS

(75) Inventors: Adrian Waldner, Allschwil (CH); Steven Mark Barnard, San Diego, CA (US)

(73) Assignee: Novartis AG, Basel (CH)

( * ) Notice: Subject to any disclaimer, the term of this patent is extended or adjusted under 35 U.S.C. 154(b) by 0 days.

(21) Appl. No.: 09/485,995

(22) PCT Filed: Aug. 14, 1998

(86) PCT No.: PCT/EP98/05167

§ 371 Date: Feb. 18, 2000

§ 102(e) Date: Feb. 18, 2000

(87) PCT Pub. No.: WO99/09406

PCT Pub. Date: Feb. 25, 1999

(30) Foreign Application Priority Data

Aug. 18, 1997 (EP) ............................................. 97810576

(51) Int. Cl.⁷ .............................................. G01N 21/64
(52) U.S. Cl. .................. 422/82.07; 422/55; 422/56; 422/82.05; 422/82.08; 436/169; 436/800; 436/111; 436/103; 436/164; 436/172; 252/501.1

(58) Field of Search ................................. 436/111, 103, 436/164, 172, 169, 800; 422/55, 56, 82.05, 82.08, 82.07; 252/501.1

(56) References Cited

U.S. PATENT DOCUMENTS 5,387,525 A    2/1995   Munkholm
5,480,611 A  * 1/1996   Mills et al. .................... 422/55

FOREIGN PATENT DOCUMENTS

| EP | 0757246  | 2/1997 |
|----|----------|--------|
| WO | 93/14399 | 7/1993 |
| WO | 96/19727 | 6/1996 |
| WO | 96/24054 | 8/1996 |

* cited by examiner

*Primary Examiner*—Jill Warden
*Assistant Examiner*—Monique T. Cole
(74) *Attorney, Agent, or Firm*—Wenderoth, Lind & Ponack, L.L.P.

(57) ABSTRACT

A sensor for the optical determination by fluorescence of carbon dioxide in liquid and gaseous media, which consist essentially of a carrier and a light-sensitive layer applied thereto. In addition to a polymer as a base substance and an anionic fluorescence dye, the light-sensitive layer also contains a quaternary onium phenolate.

19 Claims, No Drawings

OPTICAL CARBON DIOXIDE SENSORS

This application is a 371 application of PCT/EP98/05167 filed Aug. 14, 1998.

The present invention relates to sensors for the optical determination by fluorescence of carbon dioxide in liquid and gaseous media, which consist essentially of a carrier and a light-sensitive layer applied thereto, to light-sensitive compositions, to an process for the qualitative and quantitative optical determination by fluorescence of carbon dioxide in gaseous and liquid media, and to the use of sensors for the qualitative and quantitative determination of carbon dioxide in gaseous and liquid media.

The optical determination by fluorescence of carbon dioxide in gaseous and liquid media, such as air, flue gas, respiratory air, water, aqueous solutions and blood, is a valuable aid in the qualitative and quantitative determination of carbon dioxide in the said media, having in particular great diagnostic significance especially in the analysis of respiratory air and blood. The method is notable for its high sensitivity and specificity and is therefore used broadly in analysis and in particular in diagnostics.

It is known that many fluorescent dyes show no fluorescence or substantially diminished fluorescence in media of low polarity, such as non-polar solvents or polymers. Firstly, this behaviour prevents the use of these fluorescent dyes in light-sensitive layers, which consist essentially of a polymer and the fluorescent dye dispersed therein. On the other hand, it is just these light-sensitive layers and the sensors containing these light-sensitive layers that are especially desirable because of the simplicity of their production and their stability towards aqueous probes.

In U.S. Pat. No. 5,387,523, it is proposed that this problem is overcome by using the fluorescent dye together with quaternary onium compounds, the quaternary onium compounds being understood to be, as well as the quaternary ammonium compounds specifically described, also quaternary phosphonium compounds, such as tetrabutyl phosphonium bromide. On the other hand, it is emphasised that not all onium compounds act in the same way on the fluorescent dyes present in media of low polarity. The onium compounds with little or no activating action are for example n-hexadecyltributyl phosphonium bromide, tetrabutylammonium trifluormethyl sulphonate, tetrabutylammonium tetraphenyl borate, tetrabutylammonium hydrogen sulphate, tetrabutylphosphonium bromide and tetrabutylammonium bromide. At the same time, reference is made to the significance of the ion of opposite charge as a critical factor. Specifically mentioned active compounds are only tetrabutylammonium hydroxide, hexadecyl-trimethylammonium hydroxide, tetraethyl-ammonium hydroxide, tetramethylammonium hydroxide, benzyltrimethylammonium hydroxide and benzyltrimethylammonium methylate.

These quaternary hydroxides are indeed capable of activating the fluorescent of dyes in media of low polarity, but they have the disadvantage that, owing to the high basicity of the ion of opposite charge, they break down by Hofmann elimination into tertiary amine, 1-alkene and water, or by nucleophilic substitution they break down into tertiary amine and hydroxy compound. For this reason, sensors containing such a quaternary hydroxide together with a fluorescent dye in a polymer of low polarity have low stability. As a result of this, such sensor mixtures cannot be stored for a long period of time, and apparatus containing the sensors has to be constantly recalibrated, in order to compensate the change in sensitivity caused by the decomposition.

It has been found that sensors with good stability are obtained, the sensitivity of which remains constant over a considerable length of time, the sensors being storable for a long period of time, and apparatus containing the sensors does not have to be constantly calibrated, if a light-sensitive layer is applied to a carrier, the layer containing in addition to a polymer and a polyanionic fluorescent dye also a quaternary onium phenolate as activator.

A first object of the present invention is sensors for the optical determination by fluorescence of carbon dioxide in gaseous and liquid media, consisting essentially of a carrier and a light-sensitive layer applied thereto, which are characterised in that, in addition to a polymer and an anionic fluorescent dye, the light-sensitive layer contains a quaternary onium phenolate.

A quaternary phenolate preferably corresponds to formula I

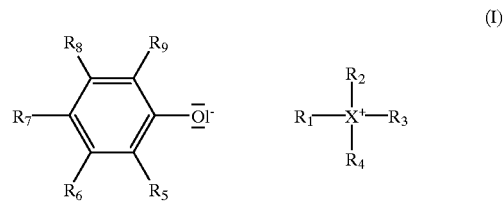

in which X is nitrogen, phosphorus or arsenic, the radicals $R_1$, $R_2$, $R_3$ and $R_4$, independently of one another, each signify straight-chain or branched, saturated or unsaturated, unsubstituted or substituted alkyl, unsubstituted or substituted aralkyl, and the radicals $R_5$, $R_6$, $R_7$, $R_8$ and $R_9$, independently of one another, each signify hydrogen, straight-chain or branched, saturated or unsaturated, unsubstituted or substituted alkyl, unsubstituted or substituted mono- or diarylalkyl or unsubstituted or substituted aryl, whereby only two of radicals $R_1$, $R_2$, $R_3$ and $R_4$ may respectively signify aryl, and 2 or 3 of radicals $R_1$, $R_2$, $R_3$ and $R_4$ may be linked together forming a heterocyclic ring system with 5–7 ring members in the individual rings, and whereby two adjacent radicals out of radicals $R_5$, $R_8$, $R_7$, $R_8$ and $R_9$ may be respectively linked together forming a saturated, unsaturated or aromatic ring with 5–7 ring members which is anellated at the phenyl radical.

In formula I, X preferably signifies nitrogen.

Halogen in the context of the invention signifies fluorine, chlorine, bromine or iodine. Halogen is preferably fluorine, chlorine or bromine, and most preferably chlorine.

The expression saturated or unsaturated alkyl includes alkyl radicals with 1 to 30 carbon atoms and the corresponding alkenyl and alkinyl radicals. For the radicals $R_1$, $R_2$, $R_3$ and $R_4$, alkyl signifies especially alkyl radicals with 1 to 8 carbon atoms and most preferably alkyl radicals with 1 to 6 carbon atoms, as well as the corresponding alkenyl and alkinyl radicals. For the radicals $R_5$, $R_6$, $R_7$, $R_8$ and $R_9$, alkyl signifies especially alkyl radicals with 1 to 10 carbon atoms and most preferably alkyl radicals with 1 to 4 carbon atoms, as well as the corresponding alkenyl and alkinyl radicals. These alkyl radicals may be mentioned by way of example: methyl, ethyl, n-propyl, isopropyl, n-butyl, isobutyl, sec.-butyl, tert.-butyl, n-pentyl, 2-methylbutyl, 3-methylbutyl, 2,2-dimethylpropyl, n-hexyl, 2-methylpentyl, 3-methylpentyl, 4-methylpentyl, 5-methylpentyl, 2-ethylbutyl, 3-ethylbutyl, n-heptyl, n-octyl, iso-octyl, n-nonyl, n-decyl, n-undecyl, n-dodecyl, n-hexadecyl, and n-octadecyl. These alkenyl radicals may be mentioned by way of example: vinyl, allyl, methallyl, 1-butenyl, 2-butenyl, 3-butenyl, 2-pentenyl, 3-pentenyl, 4-pentenyl, 2-hexenyl, 3-hexenyl, 4-hexenyl, 2-, 3-, 4-, 5- and 6-heptenyl, 2-, 3-, 4-, 5-, 6- and 7-octenyl. These alkinyl radicals may be mentioned by way of example: propargyl, 2-butinyl, 3-butinyl and 3-phenylpropargyl.

For the radicals $R_1$, $R_2$, $R_3$ and $R_4$, substituted alkyl may be especially alkyl radicals which are substituted once to three times by hydroxy, halogen, cyano, $C_1$–$C_4$-alkoxy or $C_1$–$C_4$-alkoxy-carbonyl, whereby in the case of multiple substitution, the substituents may be the same or different. For the radicals $R_5$, $R_6$, $R_7$, $R_8$ and $R_9$, substituted alkyl may be especially alkyl radicals which are substituted once to three times by hydroxy, halogen, cyano or $C_1$–$C_4$-alkoxy, whereby in the case of multiple substitution, the substituents may be the same or different.

Aryl preferably signifies phenyl or naphthyl and preferably phenyl.

For the radicals $R_1$, $R_2$, $R_3$ and $R_4$, substituted aryl may be especially aryl radicals which are substituted once to three times by $C_1$–$C_4$-alkyl, $C_1$–$C_4$-alkoxy, $C_1$–$C_4$-alkyl-$C_1$–$C_4$-alkoxy, phenyl-$C_1$–$C_4$-alkyl, halogen, halogen-$C_1$–$C_4$-alkyl, hydroxy, cyano or $C_1$–$C_4$-alkoxycarbonyl, whereby aryl preferably signifies phenyl. $C_1$–$C_4$-alkyl radicals are methyl, ethyl, n-propyl, isopropyl, n-butyl, isobutyl, sec.-butyl and tert.-butyl. Preferred phenyl-$C_1$–$C_4$-alkyl radicals, which may exist as aryl radicals as substituents of radicals $R_1$, $R_2$, $R_3$ and $R_4$, are those with 1 to 2 carbon atoms in the alkyl group, such as benzyl, 1-phenylethyl and 2-phenylethyl. Phenylalkyl signifies especially a benzyl group.

As an aralkyl group, the radicals $R_1$, $R_2$, $R_3$ and $R_4$ preferably signify an aryl-$C_1$–$C_4$-alkyl group, and most preferably a phenyl-$C_1$–$C_4$-alkyl group. As an aralkyl group, the radicals $R_1$, $R_2$, $R_3$ and $R_4$ signify in particular a phenylalkyl group with 1 to 2 carbon atoms in the alkyl group, such as benzyl, 1-phenylethyl and 2-phenylethyl. As an aralkyl group, the radicals $R_1$, $R_2$, $R_3$ and $R_4$ most preferably signify a benzyl group. As substituted aralkyl radicals, $R_1$, $R_2$, $R_3$ and $R_4$ signify especially those that are substituted once to three times in the aryl group by $C_1$–$C_4$-alkyl, $C_1$–$C_4$-alkoxy, $C_1$–$C_4$-alkyl-$C_1$–$C_4$-alkoxy, phenyl-$C_1$–$C_4$-alkyl, halogen, halogen-$C_1$–$C_4$-alkyl, hydroxy, cyano or $C_1$–$C_4$-alkoxycarbonyl. $C_1$–$C_4$-alkyl radicals are methyl, ethyl, n-propyl, isopropyl, n-butyl, isobutyl, sec.-butyl and tert.-butyl. Preferred substituted aralkyl radicals are those in which aryl represents a phenyl radical that is substituted once to three times by $C_1$–$C_4$-alkyl, $C_1$–$C_4$-alkoxy, $C_1$–$C_4$-alkyl-$C_1$–$C_4$-alkoxy, phenyl-$C_1$–$C_4$-alkyl, halogen, halogen-$C_1$–$C_4$-alkyl, hydroxy, cyano or $C_1$–$C_4$-alkoxycarbonyl, and in which the alkyl group contains 1 to 2 carbon atoms. As an aralkyl group, the radicals $R_1$, $R_2$, $R_3$ and $R_4$ most preferably signify a phenylalkyl group with 1 to 2 carbon atoms in the alkyl group, such as benzyl, 1-phenylethyl and 2-phenylethyl. As an aralkyl group, the radicals $R_1$, $R_2$, $R_3$ and $R_4$ most preferably signify a benzyl group.

For the radicals $R_5$, $R_6$, $R_7$, $R_8$ and $R_9$, substituted aryl may be especially aryl radicals which are substituted once to three times by $C_1$–$C_4$-alkyl, $C_1$–$C_4$-alkoxy, halogen, hydroxy or cyano, whereby aryl preferably signifies phenyl. $C_1$–$C_4$-alkyl radicals are methyl, ethyl, n-propyl, isopropyl, n-butyl, isobutyl, sec.-butyl and tert.-butyl.

As an aralkyl group, the radicals $R_5$, $R_6$, $R_7$, $R_8$ and $R_9$ preferably signify a mono- or diaryl-$C_1$–$C_6$-alkyl group, and most preferably a mono- or diphenyl-$C_1$–$C_6$-alkyl group. As substituted mono- or diaralkyl radicals, $R_5$, $R_6$, $R_7$, $R_8$ and $R_9$ signify especially those that are substituted in the aryl group once to three times by $C_1$–$C_4$-akyl, $C_1$–$C_4$-alkoxy, $C_1$–$C_4$-alkoxy-$C_1$–$C_4$-alkyl, halogen, halogen-$C_1$–$C_4$-alkyl, hydroxy, cyano or $C_1$–$C_4$-alkoxycarbonyl. $C_1$–$C_4$-alkyl radicals are methyl, ethyl, n-propyl, isopropyl, n-butyl, isobutyl, sec.-butyl and tert.-butyl. Preferred substituted mono- or diaralkyl radicals are those in which aryl represents a phenyl radical that is substituted once to three times by $C_1$–$C_4$-alkyl, $C_1$–$C_4$-alkoxy, $C_1$–$C_4$-alkyl-$C_1$–$C_4$-alkoxy, phenyl-$C_1$–$C_4$-alkyl, halogen, halogen-$C_1$–$C_4$-alkyl, hydroxy, cyano or $C_1$–$C_4$-alkoxycarbonyl, and in which the alkyl group contains 1 to 2 carbon atoms.

Heterocyclic ring systems, which may be formed from two or three of radicals $R_1$, $R_2$, $R_3$ and $R_4$ together with X, include for example the following structures:

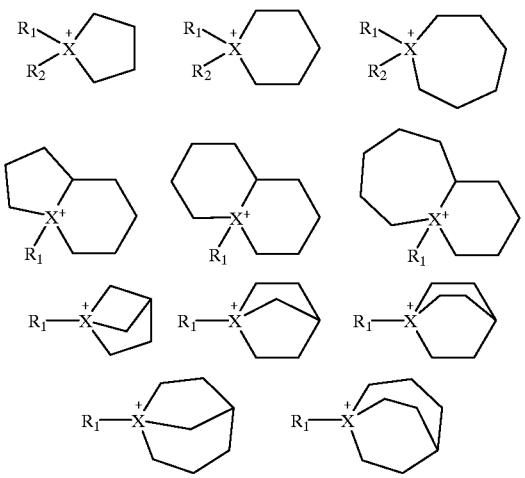

Preferred heterocyclic systems, which may be formed by joining two of radicals $R_1$, $R_2$, $R_3$ and $R_4$, are pyrrolidino, piperidino and azepino. Preferred heterocyclic systems, which may be formed from three of radicals $R_1$, $R_2$, $R_3$ and $R_4$, are 1-azabicyclo[4.3.0]nonyl, 1-azabicyclo[4.4.0]decyl, 1-azabicyclo[5.4.0]undecyl, 1-azabicyclo[2.1.1]hexyl, 1-azabicyclo[2.2.1]heptyl, 1-azabicyclo[2.2.2]octyl, 1-azabicyclo[3.2.1]octyl and 1-azabicyclo[3.2.2]nonyl.

Phenolations with an anellated saturated, unsaturated or aromatic ring formed by two adjacent radicals $R_1$, $R_2$, $R_3$ and $R_4$ include for example the following structures:

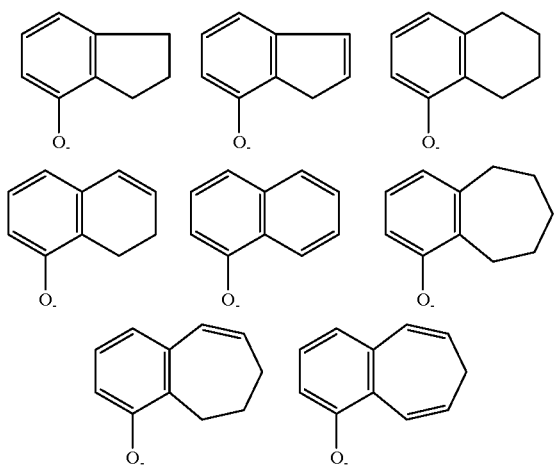

and the isomers thereof anellated in 3,4-position, whereby the significance of the radicals $R_1$, $R_2$, $R_3$ and $R_4$ not required to form the anellated ring respectively remains the same. In addition, in the anellated rings, one methylene group may be replaced by oxygen and two adjacent methylene groups may be replaced by an oxycarbonyl group and a carbonyloxy group. Preferred phenolations with an anellated saturated, unsaturated or aromatic ring contain an indanyl, indenyl, naphthyl, dihydronaphthyl or tetrahydronaphthyl radical, whereby the anellated rings may be bonded in 2,3- or 3,4-position, and the radicals $R_1$, $R_2$, $R_3$ and $R_4$ not required to form the anellated ring have the significances given under formula I.

The light-sensitive layer preferably contains a quaternary phenolate of formula I, in which X is N, P or As, $R_1$, $R_2$, $R_3$ and $R_4$, independently of one another, each signify straight-chain or branched, saturated or unsaturated, unsubstituted $C_1$–$C_{30}$-alkyl or $C_1$–$C_{30}$-alkyl substituted once to three times by $C_1$–$C_4$-alkoxy, halogen, hydroxy, cyano or $C_1$–$C_4$-alkoxycarbonyl, or unsubstituted aryl-$C_1$–$C_4$-alkyl or aryl-$C_1$–$C_4$-alkyl substituted once to three times by $C_1$–$C_4$-alkyl, $C_1$–$C_4$-alkoxy, $C_1$–$C_4$-alkoxy-$C_1$–$C_4$-alkyl, aryl-$C_1$–$C_4$-alkyl, halogen, halogen-$C_1$–$C_4$-alkyl, hydroxy, cyano or $C_1$–$C_4$-alkoxycarbonyl, or unsubstituted aryl or aryl substituted once to three times by $C_1$–$C_4$-alkyl, $C_1$–$C_4$-alkoxy, $C_1$–$C_4$-alkoxy-$C_1$–$C_4$-alkyl, aryl-$C_1$–$C_4$-alkyl, halogen, halogen-$C_1$–$C_4$-alkyl, hydroxy, cyano or $C_1$–$C_4$-alkoxycarbonyl, and $R_5$, $R_6$, $R_7$, $R_8$ and $R_9$, independently of one another, each signify hydrogen, straight-chain or branched, saturated or unsaturated, unsubstituted $C_1$–$C_{10}$-alkyl or $C_1$–$C_{10}$-alkyl substituted once to three times by halogen, $C_1$–$C_4$-alkoxy, hydroxy, cyano, or unsubstituted aryl or aryl substituted once to three times by $C_1$–$C_4$-alkyl, $C_1$–$C_4$-alkoxy, $C_1$–$C_4$-alkoxy-$C_1$–$C_4$-alkyl, halogen, halogen-$C_1$–$C_4$-alkyl, hydroxy, cyano or $C_1$–$C_4$-alkoxycarbonyl, or unsubstituted mono- or diaryl-$C_1$–$C_6$-alkyl or mono- or diaryl-$C_1$–$C_6$-alkyl substituted once to three times by $C_1$–$C_4$-alkyl, $C_1$–$C_4$-alkoxy, $C_1$–$C_4$-alkoxy-$C_1$–$C_4$-alkyl, halogen, halogen-$C_1$–$C_4$-alkyl, hydroxy, cyano or $C_1$–$C_4$-alkoxycarbonyl, whereby only two of radicals $R_1$, $R_2$, $R_3$ and $R_4$ may respectively signify aryl and 2 or 3 of radicals $R_1$, $R_2$, $R_3$ and $R_4$ may be linked together forming a heterocyclic ring system with 5–7 ring members in the individual rings, and whereby two adjacent radicals out of radicals $R_5$, $R_6$, $R_7$, $R_8$ and $R_9$ may be respectively linked together forming a saturated, unsaturated or aromatic ring with 5–7 ring members which is anellated at the phenyl radical. Preferred compounds are those in which X is nitrogen.

Further preferred are sensors which contain a compound of formula I, in which $R_1$, $R_2$, $R_3$ and $R_4$, independently of one another, each signify straight-chain or branched, saturated or unsaturated, unsubstituted $C_2$–$C_8$-alkyl or $C_2$–$C_8$-alkyl substituted once to three times by $C_1$–$C_4$-alkoxy, halogen, hydroxy, cyano or $C_1$–$C_4$-alkoxycarbonyl, or unsubstituted phenyl-$C_1$–$C_4$-alkyl or phenyl-$C_1$–$C_4$-alkyl substituted once to three times by $C_1$–$C_4$-alkyl, $C_1$–$C_4$-alkoxy, $C_1$–$C_4$-alkoxy-$C_1$–$C_4$-alkyl, halogen, halogen-$C_1$–$C_4$-alkyl, phenyl-$C_1$–$C_4$-alkyl, hydroxy, cyano or $C_1$–$C_4$-alkoxycarbonyl, or unsubstituted phenyl or phenyl substituted once to three times by $C_1$–$C_4$-alkyl, $C_1$–$C_4$-alkoxy, $C_1$–$C_4$-alkoxy-$C_1$–$C_4$-alkyl, halogen, halogen-$C_1$–$C_4$-alkyl, phenyl-$C_1$–$C_4$, hydroxy, cyano or $C_1$–$C_4$-alkoxycarbonyl, whereby only two of radicals $R_1$, $R_2$, $R_3$ and $R_4$ may respectively signify phenyl and 2 or 3 of radicals $R_1$, $R_2$, $R_3$ and $R_4$ may be linked together forming a heterocyclic ring system with 5–7 ring members in the individual rings.

Further preferred sensors according to the present invention are those which contain a compound of formula I, in which $R_1$, $R_2$, $R_3$ and $R_4$, independently of one another, each signify straight-chain or branched, saturated or unsaturated, $C_2$–$C_6$-alkyl, phenyl-$C_1$–$C_4$-alkyl or phenyl, whereby only two of radicals $R_1$, $R_2$, $R_3$ and $R_4$ may respectively signify phenyl and 2 or 3 of radicals $R_1$, $R_2$, $R_3$ and $R_4$ may be linked together forming a heterocyclic ring system with 5–7 ring members in the individual rings.

Other sensors which are preferred according to the invention contain a compound of formula I, in which $R_1$, $R_2$, $R_3$ and $R_4$, independently of one another, each signify straight-chain or branched $C_2$–$C_6$-alkyl, benzyl or phenyl.

Furthermore, according to the present invention, sensors are preferred, which contain a compound of formula I, in which $R_5$, $R_6$, $R_7$, $R_8$ and $R_9$, independently of one another, each signify hydrogen, straight-chain or branched, saturated or unsaturated, unsubstituted $C_1$–$C_4$-alkyl or $C_1$–$C_4$-alkyl substituted once to three times by halogen, $C_1$–$C_4$-alkoxy, hydroxy, cyano, or unsubstituted phenyl or phenyl substituted once to three times by $C_1$–$C_4$-alkyl, halogen, $C_1$–$C_4$-alkoxy, hydroxy, cyano, or unsubstituted mono- or diphenyl-$C_1$–$C_6$-alkyl or mono- or diphenyl-$C_1$–$C_6$-alkyl or mono- or diphenyl-$C_1$–$C_6$-alkyl substituted once to three times by $C_1$–$C_4$-alkyl, halogen, $C_1$–$C_4$-alkoxy, hydroxy, cyano.

Furthermore, according to the present invention, sensors are preferred, which contain a compound of formula I, in which $R_5$, $R_6$, $R_7$, $R_8$ and $R_9$, independently of one another, each signify hydrogen, straight-chain or branched, saturated or unsaturated $C_1$–$C_4$-alkyl, phenyl or 2-phenylethyl.

Further preferred sensors according to the present invention are those which contain a compound of formula I, in which X is N, $R_1$, $R_2$, $R_3$ and $R_4$, independently of one another, each signify straight-chain or branched, saturated or unsaturated, unsubstituted $C_2$–$C_6$-alkyl or $C_2$–$C_6$-alkyl substituted once to three times by $C_1$–$C_4$-alkoxy, halogen, hydroxy, cyano or $C_1$–$C_4$-alkoxycarbonyl, or unsubstituted phenyl-$C_1$–$C_4$-alkyl or phenyl-$C_1$–$C_4$-alkyl substituted once to three times by $C_1$–$C_4$-alkyl, $C_1$–$C_4$-alkoxy, $C_1$–$C_4$-alkoxy-$C_1$–$C_4$-alkyl, halogen, halogen-$C_1$–$C_4$-alkyl, phenyl-$C_1$–$C_4$-alkyl, hydroxy, cyano or $C_1$–$C_4$-alkoxycarbonyl, or unsubstituted phenyl or phenyl substituted once to three times by $C_1$–$C_4$-alkyl, $C_1$–$C_4$-alkoxy, $C_{1–C4}$-alkoxy-$C_1$–$C_4$-alkyl, halogen, halogen-$C_1$–$C_4$-alkyl, phenyl-$C_1$–$C_4$-alkyl, hydroxy, cyano or $C_1$–$C_4$-alkoxycarbonyl, and $R_5$, $R_6$, $R_7$, $R_8$ and $R_9$, independently of one another, each signify hydrogen, straight-chain or branched, saturated or unsaturated, unsubstituted $C_1$–$C_4$-alkyl or $C_1$–$C_4$-alkyl substituted once to three times by halogen, $C_1$–$C_4$-alkoxy, hydroxy, cyano, or unsubstituted phenyl or phenyl substituted once to three times by $C_1$–$C_4$-alkyl, halogen, $C_1$–$C_4$-alkoxy, hydroxy, cyano, or unsubstituted mono- or diphenyl-$C_1$–$C_6$-alkyl or mono- or diphenyl-$C_1$–$C_6$-alkyl substituted once to three times by $C_1$–$C_4$-alkyl, halogen, $C_1$–$C_4$-alkoxy, hydroxy, cyano.

Furthermore, according to the present invention, sensors are preferred which contain a compound of formula I, in which X is N, $R_1$, $R_2$, $R_3$ and $R_4$, independently of one another, each signify straight-chain or branched, saturated or unsaturated $C_2$–$C_6$-alkyl, phenyl-$C_1$–$C_4$-alkyl or phenyl, and $R_5$, $R_6$, $R_7$, $R_8$ and $R_9$, independently of one another, each signify hydrogen, straight-chain or branched, saturated or unsaturated $C_1$–$C_4$-alkyl, phenyl or 2-phenylethyl.

Other sensors which are preferred according to the present invention contain a compound of formula I, in which X is N, $R_1$, $R_2$, $R_3$ and $R_4$, independently of one another, each signify straight-chain or branched $C_2$–$C_6$-alkyl, benzyl or phenyl, and $R_5$, $R_6$, $R_7$, $R_8$ and $R_9$, independently of one another, each signify hydrogen, straight-chain or branched, saturated or unsaturated $C_1$–$C_4$-alkyl, phenyl or 2-phenylethyl.

The onium phenolates of formula I to be used according to the invention may possess a $pK_a$ value of between 6 and 12. Onium phenolates of formula I with a $pK_a$ value of 8 to 12 are preferred. Onium phenolates of formula I with a $pK_a$ value of 8 to 10 are especially preferred.

Transparent materials are preferably used as carrier materials for the sensors according to the invention. Suitable carrier materials are synthetic materials, such as polycarbonates or acrylic glass, or mineral materials, metal oxides or mineral glass. Preferred carrier materials are organic or mineral glass. The carrier may be of any form. Suitable forms are for example sheets, cylinders, tubes, ribbons or fibres.

The light-sensitive layer of the sensors according to the invention contains as basic substance a polymer in which are dispersed a fluorescent dye, at least one compound of formula I and optionally further additives, for example softeners. Hydrophobic polymers which are impermeable to H$^+$ ions and have a dielectricity constant of 2 to 10, preferably 2 to 6, are generally suitable. Suitable polymers in which the fluorescent dyes and the quaternary phenolates of formula I may be incorporated are in particular those which enable a transparent or slightly opaque coating to be produced on the carrier. The polymers that may be considered here are in particular acrylic polymers, such as poly-N,N-dimethylacrylamide, polyethyl acrylate, polyethyl methacrylate, polyethylhexyl acrylate and acrylic copolymers. Further appropriate polymers are polyvinyl chloride, polyvinyl acetate, polyalkenes, such as polyethylene, polypropylene, poly-(isobutene-co-isoprene), poly-(4-methylpentene), polyurethanes, cellulose derivatives, polystyrene, polytetrafluoroethylene, polyoxymethylene, polyesters, such as polyethylene terephthalate, polydienes and copolymers of dienes with acrylonitrile, such as poly-1,3-butadiene, polydimethyl butadiene, poly-(1,3-butadiene-co-acrylonitrile) and polyisoprene.

Preferred polymers are polystyrene and ethylcellulose.

The fluorescent dyes which may be considered are primarily those which display no or severely diminished fluorescence in media of low polarity. Examples of such fluorescent dyes are fluorescein, semi-naphthofluorescein, 2',7'-dimethylrhodol, HPTS (hydroxypyrene trisulphonic acid sodium salt), CASCADE BLUE (ethylenediaene pyrene trisulphonic acid sodium salt), the structures thereof are indicated below.

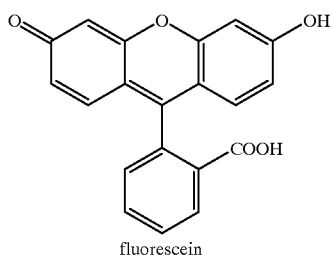
fluorescein

-continued

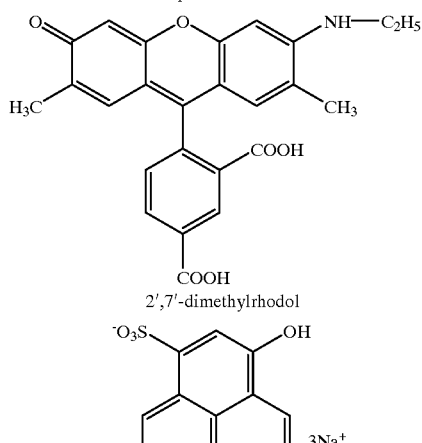
semi-naphthofluorescein

2',7'-dimethylrhodol

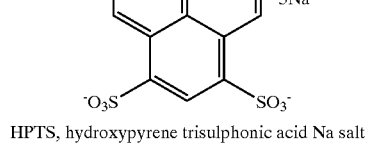
HPTS, hydroxypyrene trisulphonic acid Na salt

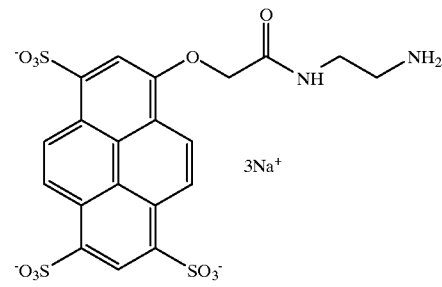
CASCADE BLUE,
ethylenediamine pyrene trisulphonic acid Na salt

Suitable softeners which may be contained in the light-sensitive layer of the sensors according to the invention are for example trialkyl phosphates, such as tributyl phosphate and octylnitrophenylether.

In the light-sensitive layer, the ratio of fluorescent dye (fluorophore) to quaternary phenolate of formula I may be from 1:500 to 1:50. The ratio of fluorophore to quaternary phenolate of formula I is preferably from 1:250 to 1:100.

The thickness of the light-sensitive layer applied to the carrier may be from 0.01 to 100 µm, preferably 0.1 to 50 µm, especially 0.1 to 30 µm, and most preferably 0.1 to 10 µm. The layer applied to the carrier may be transparent or slightly opaque. The layer is preferably transparent. Hydrophobic layers are also preferred.

Preparation of such layers may take place in a manner known per se, for example by dissolving a fluorescent dye, a compound of formula I and a suitable polymer in a solvent, then applying the solution to the carrier and removing the solvent. The solution may be applied by pouring, or by employing processes which are known from lacquering technology. Such processes which may be named are in particular spin coating, spraying and screening processes. The layers are preferably applied by the spin coating process.

The solvents which may be considered are water, alcohols, ethers, esters, acid amides, halogenated hydrocarbons and ketones. Examples of such solvents are methanol, ethanol, n-propanol, isopropanol, diethyl ether, methyl isobutyl ether, tetrahydroferan, dioxane, ethyl acetate, butyl acetate, dimethylformamide, dimethyl acetamide, methylene chloride, chloroform, acetone, methyl ethyl ketone and methyl isobutyl ketone. It is preferable to use readily volatile solvents, especially tetrahydrofuran, methylene chloride and acetone. One especially preferred solvent is tetrahydrofuran. The above-mentioned solvents may be used alone or as solvent mixtures. A viscosity of the coating compositions according to the invention which is appropriate for coating may be set by using an appropriate amount of the solvent respectively used.

The light-sensitive layer of the sensors according to the invention appears macroscopically homogeneous, but has micro-areas which are formed by the interaction between the quaternary onium ion and the polyanionic fluorescent dye. These micro-areas, the size of which lies in the region of 5 $\mu$m to 100 $\mu$m, have higher polarity than the surroundings formed by the polymer. Thus, the fluorescent dye in these micro-areas of higher polarity is protected from the fluorescence-extinguishing action of the polymer with low polarity.

A further object of the present invention is light-sensitive compositions which contain a polymer, an anionic fluorescent dye which can be activated in media of low polarity, and a quaternary phenolate of formula I as activator. For these light-sensitive compositions, the above-mentioned definitions and preferences in respect of the polymer contained therein, the fluorescent dye and the quaternary phenolate of formula I, apply accordingly. These light-sensitive compositions maybe used to produce the sensors according to the invention. They serve as coating masses for application of a light-sensitive layer to a carrier. According to one embodiment, these coating masses may exist in the form of a powder which contains an appropriate polymer, a fluorescent dye that can be activated in media of low polarity, a compound of formula I as activator and optionally further additives, in finely-dispersed form. Suitable additives are for example lipophilic salts and softeners. According to another embodiment, the coating masses may exist in the form of solutions, such as those obtained by dissolving the above-mentioned powder mixtures in one of the above-mentioned solvents.

Included among the quaternary phenolates of formula I to be used according to the invention are many known compounds.

The quaternary phenolates of formula I may be obtained in a simple manner starting with the corresponding quaternary hydroxides and reacting them with the equivalent amount of a phenol according to the following equation. The reaction is advantageously carried out in an inert solvent, for example a low alkanol, especially in methanol. When the reaction has ended, the solvent is evaporated off and the quaternary phenolate is obtained in a quantitative yield. The quaternary hydroxides required as starting materials are in turn produced in known manner from the corresponding quaternary salts, for example by reacting the quaternary halides with silver oxide.

A further object of the present invention is a process for the optical determination by fluorescence of carbon dioxide in measuring probes, in which a sensor according to the invention is brought into contact with said measuring probe to be examined and then measures the change in fluorescence of the fluorophore in the light-sensitive layer.

The process according to the invention can be carried out for example in such a way that the carrier with the active polymer layer is secured in an optical cell, in which the active layer comes into contact with the measuring probe. The optical cell contains a window, through which the active layer can be excited by illumination and the emitted fluorescence rays can be measured by a spectrofluorometer. The wavelengths can be set at the absorption maximum for illumination and the emission maximum for measuring fluorescence. Intensity is measured as a function of the concentration. The measurement system may be designed so that measurements are made discontinuously or continuously. Continuous measuring may be effected for example by pumping the liquid or gaseous analytes through the measuring cell. To determine unknown concentrations of carbon dioxide, the system can be firstly gauged with measuring probes of known concentration, whereby the intensity of fluorescence is plotted as a function of the concentration.

The invention further relates to the use of the sensors according to the invention for the qualitative and quantitative determination of carbon dioxide by fluorescence.

Through the present invention, sensors are prepared for the qualitative and quantitative determination of carbon dioxide. They are notable for their excellent stability towards aqueous probes, since the polyanionic fluorescent dyes contained in them are embedded in a hydrophobic polymer layer. In this way, when the sensor comes into contact with aqueous probes, bleeding of the dye is prevented. In addition, the sensors according to the invention possess excellent long-term stability, since as a result of the lower basicity of the phenolations used according to the invention compared with the hydroxyl ion, decomposition of the quaternary onium ions through Hofmann elimination or through nucleophilic substitution does not take place.

The invention is illustrated more fully by the following examples.

A) Production of quaternary phenolates

Example 1

Production of:

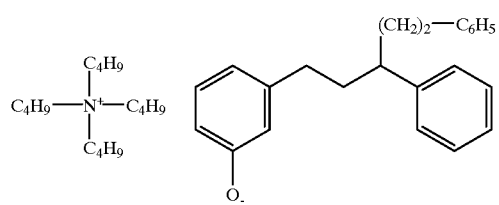

a) Production of:

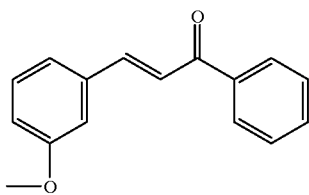

3.8 ml of a 15% aqueous solution of KOH is added dropwise at room temperature to a solution of 23.2 ml of acetophenone and 24.3 ml of 3-methoxybenzaldehyde in 120 ml of methanol. The reaction mixture is stirred over night at room temperature and then acidified by adding 100 ml of 2n HCl. After evaporating the methanol, the aqueous residue is extracted three times with ether. The organic phase is washed with water and sodium chloride solution, dried over $MgSO_4$ and the solvent evaporated. The crude product is purified by distillation under a high vacuum. $Bp_{0.055\ mbar}$: 162° C.; yield: 30.4 g (64% of theory).

b) Production of:

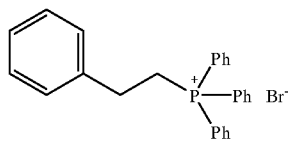

6.9 g of triphenylphosphine and 5.0 g of 2-phenylethylbromide are dissolved in 35 ml of toluene and heated under reflux for 24 hours. Then the solvent is evaporated and the crystalline residue is purified with ether. Yield: 93% of theory.

c) Production of:

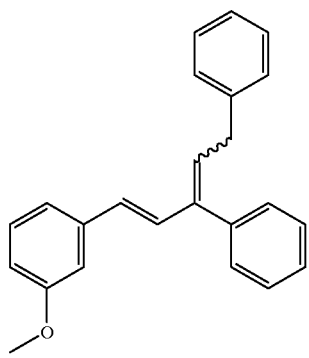

To a suspension of 4.5 g of the phosphonium bromide produced according to b) in 120 ml of absolute tetrahydrofuran are added dropwise under argon, at −180° C., 8.2 ml of a 1.6 molar solution of butyllithium. To the clear solution obtained is added a solution of 2.4 g of the compound of example 1a in 20 ml of absolute tetrahydrofuran. The reaction mixture is heated to room temperature and stirred for 4 days. Then, water and ether are added and the organic phase is separated, washed with sodium chloride solution, dried and concentrated by evaporation. The oily residue is chromatographed on silica gel using $CH_2Cl_2$/hexane as eluant.

Yield: 1.85 g (57% of theory); $^1$H-NMR ($CDCl_3$): 3.35 (m, 2H, $CH_2$); 3.78 (s, 3H, $OCH_3$); 6.0–6.1 (m, 2H, 2 C=CH).

d) Production of:

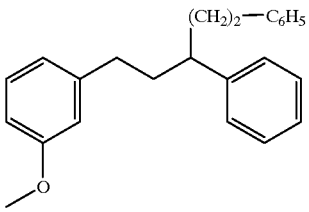

0.5 g of the compound produced according to c) and 0.05 g of Pd on carbon (10%) in 15 ml of tetrahydrofuran are stirred vigorously for 12 hours in a hydrogen atmosphere. Then, the reaction mixture is filtered and the filtrate evaporated to dryness, whereby the desired product is obtained in a quantitative yield. $^1$H-NMR ($CDCl_3$): 1.80–2.05 (m, 4H, 2 $CH_2$); 2.35–2.50 (m, 4H, 2 $CH_2$); 2.55–2.65 (m, 1H, CH); 3.78 (s, 3H, $OCH_3$); 6.60–7.40 (m, 14 arom. H).

e) Production of:

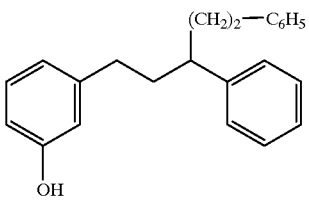

7.83 g of the compound produced according to d) are dissolved in 200 ml of dichloromethane, and cooled to −78° C. 3.4 ml of boron tribromide are added dropwise to this solution. The reaction mixture is stirred for 17 hours at room temperature and poured onto ice. After setting the pH value of the mixture to 1, extracting with ether, washing with sodium chloride solution, drying with $MgSO_4$ and evaporating the solvent, the crude product obtained is purified by flash chromatography on silica gel using dichloromethane/hexane (1:1) as eluant. MS: 316.

f) Production of tetrabutylammonium[3-(3,5-diphenylpentyl)phenolate]:

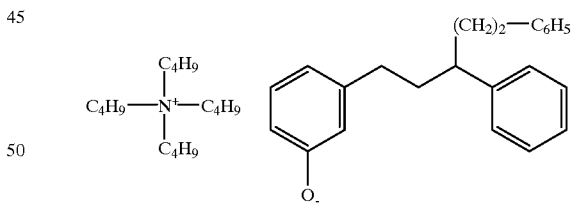

To 10 ml of a fresh 1M solution of tetrabutylammonium hydroxide in methanol are added 10 mmols of the phenol produced according to e). The solution obtained is evaporated to dryness. The crystalline compound obtained is washed with ether and dried at 40° C. Yield: quantitative.

Other quaternary phenolates may be produced in analogous manner. If oily products are obtained, these are advantageously dried at 40° C. in a bulb-tube oven.

B) Stability test

An investigation is carried out as to the extent to which tetrabutylammonium hydroxide and tetrabutylammonium-p-methylphenolate in solution decompose to tributylamine, 1-butene and water or phenol (X=H or p-methylphenyl), depending on time, by Hofmann elimination according to the equation

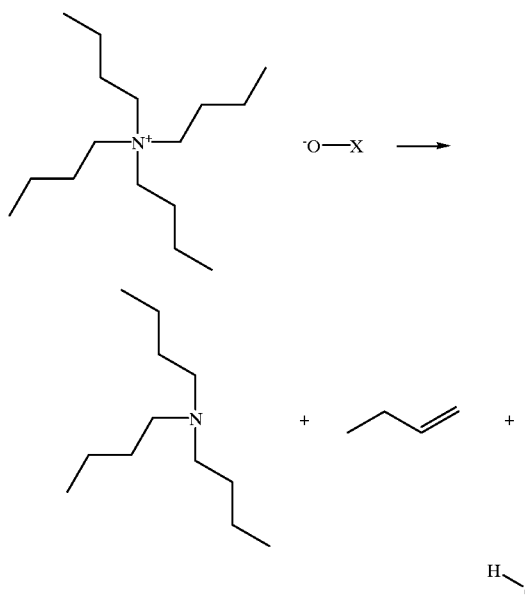

A $3 \cdot 10^{-2}$ molar solution of each test substance in perdeuterotoluene is prepared. To 1 ml of each of these solutions is added 160 all of a solution of hydroxypyrene-tri-Na-sulphonate (HPTS) with a content of 1 mg/ml HPTS (1.91 mM) per ml. A sample of each of the solutions thus prepared is sealed in a NMR tube and stored at 35° C. Decomposition of the substances is determined by NMR spectroscopic analysis of the measuring probes over a period of in all 52 days, whererby, in addition to the appearance of the whole NMR spectrum, a criterion for decomposition is the formation of tributylamine detected by its characteristic signals. The measurements are summarised in the following table, whereby the percentages indicate the amount of resulting tributylamine in relation to the original amount present.

| | degree of decomposition (%) | |
|---|---|---|
| time (days) | tetrabutylammonium hydroxide | tetrabutylammonium-p-methyl-phenolate |
| 0 | 0 | 0 |
| 7 | traces | 0 |
| 23 | 6 | 0 |
| 35 | 12 | 0 |
| 52 | 16 | 0 |

C) Production of Sensors a) Tetrabutylammonium phenolate in polystyrene

A stock solution of the polymer is produced by dissolving 600 mg of polystyrene (catalogue no. 039A from Scientific Polymer Products, Inc, USA) in 6 ml of tetrahydrofuran (content: 6%). In addition, by dissolving 6.6 mg of 8-hydroxypyrene-1,3,6-trisulphonic acid trisodium salt, HPTS, (Molecular Probes, Inc., Oregon, USA) in 5 ml of methanol ($2,5 \cdot 10^{-3}$ mol/l), a stock solution of the flurophore is produced, and by dissolving 150 mg of tetrabutylammonium phenolate in 0.3 ml (1 molar solution), a stock solution of the quaternary phenolate is produced. Then, by adding 0.067 ml stock solution of the fluorophore and 0.042 ml of the stock solution of the quaternary phenolate to 2 ml of the stock solution of the polymer, a starting solution is produced for coating in the spin-coating process, in a concentration of $8,37 \cdot 10^{-5}$ mol/l of HPTS and $2,09 \cdot 10^{-2}$ mol/l of quaternary phenolate. 0.2 ml of this solution are removed and added using a pipette to a purified round cover glass with a diameter of 18 mm. The cover glass is spun first of all for 20 seconds at 2000 rpm and then for 30 seconds at 9000 rpm. The sensors are protected from light and dried over night at room temperature. The following table gives the results of measurement obtained with the sensor.

| % $CO_2$ | intensity of fluorescence |
|---|---|
| 2.7 | 319 |
| 5.3 | 273 |
| 8.7 | 252 | b) Tetrabutylammonium[3-(3,5-diphenylpentyl) phenolate] (compound f) in polystyrene A stock solution of the polymer is produced by dissolving 600 mg of polystyrene (catalogue no. 039A from Scientific Polymer Products, Inc, USA) in 6 ml of tetrahydrofuran (content: 6%). In addition, by dissolving 6.6 mg of 8-hydroxypyrene-1,3,6-trisulphonic acid trisodium salt, HPTS, (Molecular Probes, Inc., Oregon, USA) in 5 ml of methanol ($2,5 \cdot 10^{-3}$ mol/l), a stock solution of the fluorophore is produced, and by dissolving 167 mg of tetrabutylammonium[3-(3,5-diphenyl pentyl) phenolate] in 0.3 ml (1 molar solution), a stock solution of the quaternary phenolate is produced. Then, by adding 0.067 ml of stock solution of the fluorophore and 0.042 ml of the stock solution of the quaternary phenolate to 2 ml of the stock solution of the polymer, a starting solution is produced for coating in the spin-coating process, in a concentration of $8,37 \cdot 10^{-5}$ mol/l of HPTS and $2,09 \cdot 10^{-2}$ mol/l of quaternary phenolate. 0.2 ml of this solution are removed and added using a pipette to a purified round cover glass with a diameter of 18 mm. The cover glass is spun first of all for 20 seconds at 2000 rpm and then for 30 seconds at 9000 rpm. The sensors are protected from light and dried over night at room temperature. The following table gives the results of measurement obtained with the sensor.

| % $CO_2$ | intensity of fluorescence |
|---|---|
| 2.7 | 261 |
| 5.3 | 220 |
| 8.7 | 197 | c) Tetrabutylammonium phenolate in ethyl cellulose

The sensor is produced analogously to the above-described procedure, with the exception that a 5% solution of ethyl cellulose is used as the stock solution for the polymer. The solution is produced by dissolving 300 mg of ethyl cellulose (Aldrich, Milwaukee, Wis. USA) in 6 ml of tetrahydrofuran.

| % $CO_2$ | intensity of fluorescence |
|---|---|
| 2.7 | 319 |
| 5.3 | 273 |
| 8.7 | 252 | d) Tetrabutylammonium[3](3,5-diphenylpentyl)-phenolate] in ethyl cellulose

The sensor is produced analogously to the above-described procedure, with the exception that a 5% solution of ethyl cellulose is used as the stock solution for the polymer. The solution is produced by dissolving 300 mg of ethyl cellulose (Aldrich, Milwaukee, Wis. USA) in 6 ml of tetrahydrofuran.

| % $CO_2$ | intensity of fluorescence |
|---|---|
| 2.7 | 261 |
| 5.3 | 220 |
| 8.7 | 197 |

What is claimed is:

1. Sensor for the optical determination by fluorescence of carbon dioxide in gaseous and liquid media, consisting essentially of a carrier and a light-sensitive layer applied thereto, characterised in that in addition to a polymer as base substance and an anionic fluorescent dye, the light-sensitive layer also contains a quaternary onium phenolate.

2. Sensor according to claim 1, characterised in that in addition to a polymer as base substance and an anionic fluorescent dye, the light-sensitive layer also contains a quaternary ammonium phenolate.

3. Sensor according to one of claims 1 or 2, characterised in that in addition to a polymer as base substance and an anionic fluorescent dye, the light-sensitive layer also contains a quaternary onium phenolate of formula I

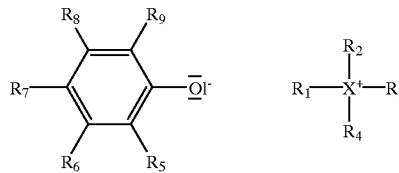

(I)

in which in which X is nitrogen, phosphorus or arsenic, the radicals $R_1$, $R_2$, $R_3$ and $R_4$, independently of one another, each signify straight-chain or branched, saturated or unsaturated, unsubstituted or substituted alkyl, unsubstituted or substituted aralkyl, and the radicals $R_5$, $R_6$, $R_7$, $R_8$ and $R_9$, independently of one another, each signify hydrogen, straight-chain or branched, saturated or unsaturated, unsubstituted or substituted alkyl, unsubstituted or substituted mono- or diarylalkyl or unsubstituted or substituted aryl, whereby only two of radicals $R_1$, $R_2$, $R_3$ and $R_4$ may respectively signify aryl, and 2 or 3 of radicals $R_1$, $R_2$, $R_3$ and $R_4$ may be linked together forming a heterocyclic ring system with 5–7 ring members in the individual rings, and whereby two adjacent radicals out of radicals $R_5$, $R_6$, $R_7$, $R_8$ and $R_9$ may be respectively linked together forming a saturated, unsaturated or aromatic ring with 5–7 ring members which is anellated at the phenyl radical.

4. Sensor according to claim 3, characterised in that X is nitrogen.

5. Sensor according to claim 1, characterised in that the carrier consists of a transparent material.

6. Sensor according to one of claims 1, 2 or 5, characterised in that the carrier consists of a synthetic material selected from polycarbonates or polyacrylates.

7. Sensor according to claim 1, characterised in that the light-sensitive layer contains as basic substance a polymer which is selected from the group comprising acrylic polymers, acrylic copolymers, polyvinyl chloride, polyvinyl acetate, polyethylene, polypropylene, poly-(isobutene-co-isoprene), poly-(4-methylpentene), polyurethanes, cellulose derivatives, polystyrene, polytetrafluoroethylene, polyoxymethylene, polyesters, polydienes, copolymers of dienes with acrylonitrile, and polyisoprene.

8. Sensor according to one of claims 1, 2, 5 or 7, characterised in that the light-sensitive layer contains as basic substance a polymer which is selected from the group comprising polystyrene and ethyl cellulose.

9. Light-sensitive composition, characterised by a content of a polymer as basic substance, an anionic fluorescent dye that can be activated in media of low dielectricity constant, and a quaternary onium phenolate as activator.

10. Process for the optical determination by fluorescence of carbon dioxide in measuring probes, characterised in that a sensor according to one of claims 1, 2, 5 or 7 is brought into contact with the measuring probe and then measures the change in fluorescence of the anionic fluorescent dye in the light-sensitive layer, whereby the intensity of fluorescence is measured as a function of the concentration.

11. Sensor according to claim 3, characterised in that the carrier consists of a synthetic material selected from polycarbonates or polyacrylates.

12. Sensor according to claim 4, characterised in that the carrier consists of a synthetic material selected from polycarbonates or polyacrylates.

13. Sensor according to claim 3, characterised in that the light-sensitive layer contains as basic substance a polymer which is selected from the group comprising polystyrene and ethyl cellulose.

14. Sensor according to claim 4, characterised in that the light-sensitive layer contains as basic substance a polymer which is selected from the group comprising polystyrene and ethyl cellulose.

15. Sensor according to claim 6, characterised in that the light-sensitive layer contains as basic substance a polymer which is selected from the group comprising polystyrene and ethyl cellulose.

16. Process for the optical determination by fluorescence of carbon dioxide in measuring probes, characterised in that a sensor according to claim 3 is brought into contact with the measuring probe and then measures the change in fluorescence of the anionic fluorescent dye in the light-sensitive layer, whereby the intensity of fluorescence is measured as a function of the concentration.

17. Process for the optical determination by fluorescence of carbon dioxide in measuring probes, characterised in that a sensor according to claim 4 is brought into contact with the measuring probe and then measures the change in fluorescence of the anionic fluorescent dye in the light-sensitive layer, whereby the intensity of fluorescence is measured as a function of the concentration.

18. Process for the optical determination by fluorescence of carbon dioxide in measuring probes, characterised in that a sensor according to claim 6 is brought into contact with the measuring probe and then measures the change in fluorescence of the anionic fluorescent dye in the light-sensitive layer, whereby the intensity of fluorescence is measured as a function of the concentration.

19. Process for the optical determination by fluorescence of carbon dioxide in measuring probes, characterised in that a sensor according to claim 8 is brought into contact with the measuring probe and then measures the change in fluorescence of the anionic fluorescent dye in the light-sensitive layer, whereby the intensity of fluorescence is measured as a function of the concentration.

* * * * *